US012637655B2

(12) United States Patent
Brantes Bacellar Mendes et al.

(10) Patent No.: US 12,637,655 B2
(45) Date of Patent: May 26, 2026

(54) MASSIVE CO₂ BIOFIXATION PROCESS AND SEAWEED BIOMASS PRODUCTION WITH THE USE OF GRAVELS FROM OIL WELL DRILLING

(71) Applicant: Petróleo Brasileiro S.A.—Petrobras, Rio de Janeiro (BR)

(72) Inventors: Leonardo Brantes Bacellar Mendes, Rio de Janeiro (BR); Heraldo Namorato De Souza, Rio de Janeiro (BR); Ronaldo Bernardo Da Silva, Rio de Janeiro (BR); Rafael Richard Joao, Rio de Janeiro (BR)

(73) Assignee: Petróleo Brasileiro S.A.—Petrobras, Rio de Janeiro (BR)

( * ) Notice: Subject to any disclaimer, the term of this patent is extended or adjusted under 35 U.S.C. 154(b) by 615 days.

(21) Appl. No.: 18/177,880

(22) Filed: Mar. 3, 2023

(65) Prior Publication Data
US 2023/0323278 A1 Oct. 12, 2023

(30) Foreign Application Priority Data
Mar. 31, 2022 (BR) ...................... 10 2022 006198 0

(51) Int. Cl.
*C12N 1/12* (2026.01)
*A01G 33/00* (2006.01)
(Continued)

(52) U.S. Cl.
CPC .............. *C12N 1/12* (2013.01); *A01G 33/00* (2013.01); *B09B 3/60* (2022.01); *C05D 9/02* (2013.01)

(58) Field of Classification Search
CPC ....... C02F 2103/10; C12N 1/12; A01G 33/00; B09B 3/60
See application file for complete search history.

(56) References Cited

U.S. PATENT DOCUMENTS

2019/0241847 A1 8/2019 Krivov

OTHER PUBLICATIONS

"Strain (biology)", Wikipedia, screen capture saved by the Wayback Machine on Jan. 21, 2022. (Year: 2022).*
(Continued)

*Primary Examiner* — Daniel E Kolker
*Assistant Examiner* — Amelia Nicole Dickens
(74) *Attorney, Agent, or Firm* — Morrison & Foerster LLP

(57) ABSTRACT
The present invention relates to the direct use by addition of drilling gravels residue from the oil exploration and production activities in the formulation of culture medium of unicellular organisms, increasing its growth rates, intensifying the CO₂ biofixation, and generating value to this residue from of productivity gains expected by autotroph and mixotroph organisms (cyanobacteria, microalgae and macroalgae), as well as the production of bioproducts that can be generated through the concept currently described in the literature as biorefining. Algae are cultured using drilling gravel suspended in the culture medium together with the ability to grow by absorbing CO₂. Mechanisms used by algae in soils and marine environments to tolerate salinity, sodicity and contamination of petroleum hydrocarbons provides wide adaptation to these conditions of abiotic stress and enables the destination without environmental impact, constituting a satisfactory solution for the destination of the gravel for oil exploration and production.

10 Claims, 5 Drawing Sheets

(51) Int. Cl.
 *B09B 3/60* (2022.01)
 *C05D 9/02* (2006.01)

(56) References Cited

OTHER PUBLICATIONS

"Seaweed", Wikipedia, screen capture saved by the Wayback Machine on Feb. 2, 2022. (Year: 2022).*

Kovaleva et al. "Drill cuttings in the environment: possible ways to improve their properties", published online Sep. 29, 2020, Journal of Soils and Sediments, vol. 21 (2021), pp. 1974-1988. (Year: 2020).*

Mahdavi et al. "Metal removal from oil sands tailings pond water by indigenous micro-alga", Sep. 2012, Chemosphere, vol. 89, Issue 3, pp. 350-354 (Year: 2012).*

Sivasubramanian et al. "Large scale phycoremediation of oil drilling effluent", 2012, Journal of Algal Biomass Utilization, 3 (4): p. 5-17. (Year: 2012).*

Fontes, Luiza Moura (2017) "Biodegradation of Heavy Waste Oil Emulsion in *Desmodesmus* Sp. (Avaliação Ecotoxicológica Da Eficácia De Tratamentos De Resíduos De Mineração E Perfuração De Poços De Petróleo)", Universidade Federal Da Bahia Escola Politécnicaprograma De Pós-graduação Em Engenharia Industrial, 92 pages (English Abstract Submitted).

Roldão et al. (2016) "Ecotoxicological Evaluation of Waste Treatment Effectiveness From Mining and Oil Drilling Activities (Biodegradação De Emulsão De Óleo Residual Pesado Em Cultivo De *Desmodesmus* Sp.)", In: Jornada Do Programa De Capacitação Interna Do Cetem, 5. Rio De Janeiro. Anais. Cetem/mctic, 7 pages (English Abstract Submitted).

* cited by examiner

MASSIVE CO$_2$ BIOFIXATION PROCESS AND SEAWEED BIOMASS PRODUCTION WITH THE USE OF GRAVELS FROM OIL WELL DRILLING

CROSS-REFERENCE TO RELATED APPLICATION

This application claims priority to Brazilian Application No. 10 2022 006198 0, filed on Mar. 31, 2022, and entitled "MASSIVE CO2 BIOFIXATION PROCESS AND SEAWEED BIOMASS PRODUCTION WITH THE USE OF GRAVELS FROM OIL WELL DRILLING," the disclosure of which is incorporated herein by reference in its entirety.

FIELD OF THE INVENTION

The present invention relates to a massive CO$_2$ biofixation process through the addition of drilling gravel from oil exploration and production activities in the formulation of algae culture medium. This process contributes to increased productivity of biomass of cyanobacterial, microalgae and macroalgae culture systems, collaborating for economic viability of the obtained bioproducts and/or bioinputs (for example, biofertilizers, additives for use in mineral fertilizers, vegetable biostimulants, organic binder agents and complexants, nutraceuticals, biofuels) with the reduction of the required culture area and equipment associated with the process, as well as the required labor force.

DESCRIPTION OF THE STATE OF THE ART

Solid waste produced in oil well drilling activities constitute a liability environment that imply high costs to the exploration and production activities due to the need for the correct destination according to existing environmental regulations, in addition to subject to the permanent risk of receiving possible fines and/or legal nature embargoes, without expectation of some financial return or possible valuation of this material.

Currently, it is estimated that the amount of drilling gravel generated by offshore exploration and production activities that is landed for treatment and destination on land corresponds to about 50 ton/year in the offshore units of Petrobras, being composed of a contingent of gravel adhered with water-based fluid contaminated with oil from geological formations and other origins and all the gravel adhered with the non-aqueous base fluids. The remainder of the drilling gravels produced is discarded at sea, as long as it does not comply with the current environmental standards.

With the publication of the Normative Instruction #1 of the Brazilian Institute of Environment and Renewable Natural Resources (IBAMA) 2018, currently suspended on appeal lodged by the ANP, there was an estimation to reduce the disposal of drilling gravels at sea until deployment of the total ban on disposal in the marine environment, passing by an intermediate phase with the collection of gravel from the reservoir phase of drilling wells. So, in the first phase, all the gravel should be forwarded from the reservoir phase— something around 17 thousand tons/year, and in the second phase, zero disposal, all gravel generated during the well drilling should be collected—something in around 70 thousand tons/year. These estimates were made in the year 2019, for Petrobras offshore units. Its about a significant and characteristic amount of waste without technological alternative of viable treatment and whose possible current destination would be disposal in industrial landfills, with major impacts on the soil and aquifers.

It should be emphasized that the company would legally continue jointly and severally liable for the costs of any accidents and environmental impacts associated with disposal in industrial landfills. Add to this the logistical, technical and economic challenges that need to be confronted and overcome.

When drilling oil wells, large volumes of drilling gravel are produced, which require treatment and destination for proper disposal in the environment, reuse or recycling. The composition of drilling gravel depends on the type of drilling fluid used and the mineralogical composition of the rocks drilled during well drilling and construction.

Improper treatment and disposal of gravel can trigger several environmental impacts, such as, for example, salinization, sodization and soil and aquifer contamination due to the high levels of salts and sodium and eventual high levels of oil hydrocarbons.

Greenhouse gas emissions by "carbon intensive" industries have a great impact on climate changes. Companies that seek environment sustainability look for solutions to mitigate their emissions, through "afterburning" strategies, as most of "direct" CO$_2$ fixation technologies, which have worst cost/benefit ratios compared to indirect alternatives, such as CO$_2$ biofixation.

There is currently no plausible utility or function of drilling waste in biotechnological processes that can collaborate with the transition to a low carbon economy. This scenario can be changed with the application of these residues in biotechnological processes that perform CO$_2$ biofixation, with increased production of biomass by photosynthetic organisms (cyanobacteria, microalgae or macroalgae) and conversion into advanced biofuels, bioproducts and/or bioinputs, commodities from chemical industry and high added value products.

Cyanobacteria, microalgae or macroalgae have CO$_2$ biofixation capacity in its biomass. From all the photosynthetic organisms, these are the biggest fixers of CO$_2$ and can capture large amounts of this compound. They represent one of the most promising alternatives for tackling global warming, being able to remove CO$_2$ from gaseous streams, as they can support levels of up to 50% CO$_2$, as well as the presence of other polluting and toxic compounds to other photosynthetic organisms, such as NO$_x$ and SO$_2$.

Compared to trees, which have the capacity to CO$_2$ fixation estimated at around 1 t·ha$^{-1}$·year$^{-1}$, which may reach 3.5 t·ha$^{-1}$·year$^{-1}$ in tropical forests such as Brazil, cyanobacteria, microalgae or macroalgae can fix 6.3 t·ha$^{-1}$·year$^{-1}$, reaching 16.2 t·ha$^{-1}$·year$^{-1}$ in tropical regions, which make up most part of Brazil. The fast growth of these organisms and the wide tolerance to extreme abiotics factors, allow its culture in a few days, in brackish, salty waters, or even unsuitable for other activities, such as agriculture, not competing with the food production and water supply. Sectors like cement production, steel industry and thermoelectric power generation using fossil fuels and the oil and gas sector itself can benefit from strategies to CO$_2$ biofixation by cyanobacteria, microalgae or macroalgae.

The biomass of cyanobacteria, microalgae or macroalgae can be used in the production of advanced biofuels, such as renewable hydrocarbons, biodiesel or 2$^{nd}$ generation ethanol. In addition to this aforementioned use, the seaweed biomass can be used for the production of drilling fluid, biolubricants, antioxidants, biohydrogen, biopolymers, functional foods, nutritional supplements, pharmaceutical, cosmetics, nutraceuticals, in addition to biological detoxification of liquid effluents and solid waste from industrial, agro-industrial and home care origin, among other possibilities not mentioned.

FONTES, L. M. (2017) "Biodegradação de emulsão de óleo residual pesado em cultivo de *Desmodesmus* sp", 91f., Dissertation (Master in Industrial Engineering)—Escola Politécnica, Federal University of Bahia, Salvador, describes a study on the ability of microalgae from species *Desmodesmus* sp. to biodegrade heavy residual oil emulsions (BPF) in water. Emulsions with biodegradable anionic and non-ionic surfactants were prepared, allowing microalgae access to aqueous culture to residual oil and its toxic components, polycyclic aromatic hydrocarbons (PAHs). Along each experiment the cellular growth of the microalgae was evaluated and accompanied the carotenoid contents of the cultures through Raman spectroscopy. In the end, the presence of PAHs in the culture medium was evaluated through gas chromatographic technique. The species *Desmodesmus* sp. showed an atypical growth curve in the presence of emulsified BPF oil, as well as alterations in the metabolism of β-carotene production. It was concluded that microalgae from species *Desmodesmus* sp. were able to biodegrade in 90 days, under the conditions used in the experiments, the organic components present in BPF oil, including most PAHs present.

Document US 20190241847 A1 discloses a culture system and algae growth that provides a biomass producing low cost medium as a raw material for algae-based products, such as the manufacture of biofuel and, desirably, impacts the production of alternative/renewable energy, waste streams nutrient recovery and the production of valuable by-products. The system presents an integrated systems approach to wastewater treatment, selection of algae strains for the production of by-products and recycling of algae oil extraction or additional algae harvested as raw material for the production of fertilizers. The work comprises an integrated system approach to wastewater treatment, selection of algae strains for oil production, $CO_2$ capture, or capture of nutrients from heterotrophic processes and recycling of algae oil extraction residues as raw material for the production of biogas.

ROLDÃO, T. M.; EGLER, S. G. (2016) "Avaliação ecotoxológica da eficácia de tratamento de resíduos de mineração e perfuração de poços de petróleo", V Jornada do Programa de Capacitação Interna—CETEM, discloses an evaluation study on the effectiveness of treatments for adequate disposition and/or use of mining residues from coal and onshore oil well drilling, through ecotoxicological tests. Acute and chronic assays were done with marine or land organisms and escape with oligochaetes. The crude residue of coal sample was more toxic than the treated one in all tests carried out. The same occurred in the tests carried out with the drilling gravels samples, in which the samples processed in the Phase 1 Dryer were more toxic than those of the Phase 2 Dryer. The treatment performed on the tested samples were effective for reducing toxicity; however, the analyzes performed up to the present moment have demonstrated that the residues treated still cause toxic effects on the tested organisms.

No document from the state of the art searched discloses a guarantee of survival of microalgae in medium with drilling gravel, even less about the best performance in terms of growth. In this way, the present invention takes care to protect this discovery, which can be amplified not only for offshore drilling gravel of the pre-salt layer, but also for offshore drilling gravel from other geological layers, such as the Post-Salt, the onshore gravel, and any other waste arising from oil exploration and production activities that have in their compositions materials from the fractions of rocks of geological formation obtained during the drilling and construction process of oil wells, and can be associated or not with any types and purposes of oil drilling fluids.

The drilling gravel in principle represents an environmental liability for oil companies, resulting in cost in various forms. The prospect for the near future is that it be destined as waste with all transportation, storage and other costs associated.

Thus, the present invention allows the use of this residue as a special component for culture medium applied on onshore sites, which have $CO_2$ streams that need to be slaughtered or valued. An offshore application is unlikely, whatever the unit operations not directly related to drilling activities. In this way, the contaminated gravel or could not be used in the algae culture tanks, in the $CO_2$ streams of the Natural Gas Processor Units (NGPUs), or in Refineries or Thermoelectric Plants (UTEs), thus contributing to the mitigation of $CO_2$ and with the general process of microalgae production.

It should have in mind that there is a cost with the distribution of $CO_2$ from the unit to the place of culture of the microalgae. The costs of harnessing $CO_2$ from an enriched source depend on location, capture methods, and the distance to pump the gas to the culture system of microalgae. Therefore, for this strategy to be viable, the industrial microalgae culture plant must be located close to or within the same unit, if space is available.

The present invention leads to the increase of productivity of cyanobacterial, microalgae and macroalgae culture systems, contributing to the economic viability of bioproducts and/or bioinputs obtained, such as biostimulants, nutraceuticals, and biofuels, among others mentioned above, by reducing the culture area and equipment necessary for the process, as well as the required labor force.

A bioinput is the product, process, or technology of plant, animal or microbial origin, intended for use in the production, storage, and improvement of agricultural products, in the systems of marine production or planted forests, which positively interfere on growth, development, and response mechanism of animals, plants, microorganisms, and substances derived from and interacting with physical-chemical and biological products and processes, as defined by the legal text of the Decree #10,375, of May 26, 2020, of the Bioinputs Legislation.

Consequently, the use of solid waste arising from oil exploration and production activities and gas for biomass production and intensive biofixation of $CO_2$ can reduce or even eliminate drilling waste disposal in industrial landfills, minimizing the difficulties related to the collection, transport and treatment of waste, in addition to avoiding the cost of industrial landfills.

BRIEF DESCRIPTION OF THE INVENTION

The present invention relates to a massive $CO_2$ biofixation process through the addition of drilling gravel from oil exploration and production activities in the formulation of microalgae, cyanobacteria and macroalgae culture medium, increasing their growth rates, intensifying $CO_2$ biofixation, and generating value to this waste based on productivity gains from biomass expected by autotrophic and mixotrophs organisms (cyanobacteria, microalgae and macroalgae), as well as the production of bioproducts or bioinputs that can be generated through the concept currently described in the literature as biorefining.

BRIEF DESCRIPTION OF THE DRAWINGS

The present invention will be described in more details below, with reference to the attached figures which, in a schematic and non-limiting of the inventive scope, represent examples of their achievement. In the drawings, there are.

DETAILED DESCRIPTION OF THE INVENTION

Figure 1:
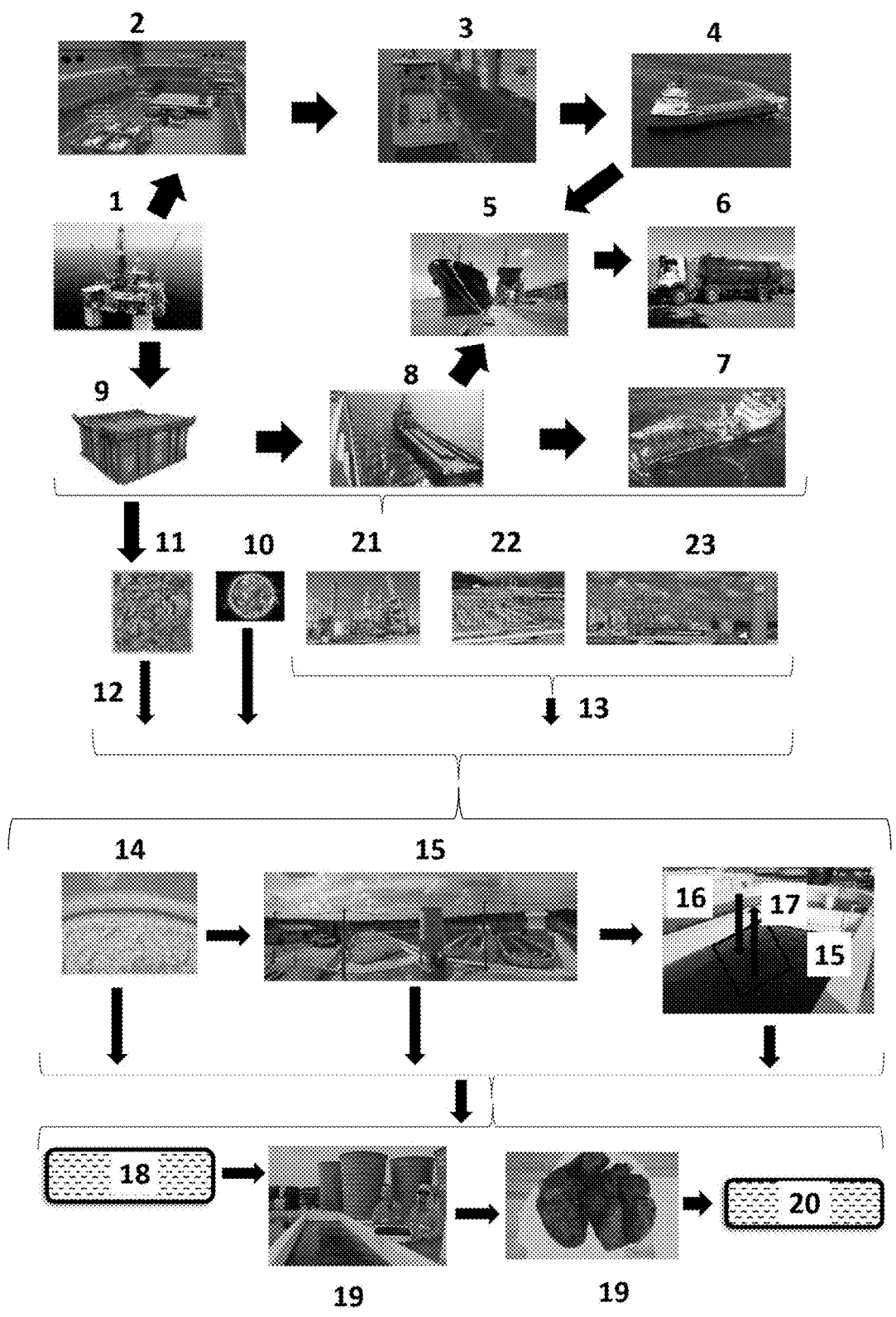
FIG. 1 illustrating the drilling gravel collection streams, the necessary logistical resources, and the massive $CO_2$ biofixation process and biomass production by cyanobacteria, microalgae, or macroalgae, according to the present invention.

The massive $CO_2$ biofixation process and algal seaweed biomass production, according to the present invention and illustrated in FIG. 1, comprises a conventional culture medium, oil drilling gravel, aeration bubbling, cyanobacterial, microalgae, or macroalgae culture and a pH regulator with trigger of $CO_2$ by solenoid valve.

According to FIG. 1, considering all the offshore gravel collection scenarios, whether from actuality, whether from the reservoir phase, and zero disposal, in the gravel collection system (2) in the probe (1), the gravel associated or not with discarded drilling fluids is transferred directly to gravel/hybrid boats (3). The gravel/hybrid boats sail (4) to the receiving ports and berth for gravel unloading (5). Finally, they go by land transport (6) to be used in the formulation of algae culture medium.

Another form of transporting gravel associated or not to discarded drilling fluids is through the packaging in cutting box (9) on adapted transport boats (8) sailing (7) to receiving ports and berth for gravel unloading (5) and from there follow the same unpackaged transport route previously described.

Solar radiation (10) affects culture tanks (15) of seaweed biomass production, where they are placed cyanobacteria, microalgae or macroalgae inoculums (14) containing water and culture medium (12), adding drilling gravel (11) and $CO_2$ (13) supplied from refineries (21), natural gas processing units (NGPUs) (22) and thermoelectric plants (UTEs) (23), which are consumed at a rate of 60 g of $CO_2/m^2/day$ (16) and produce and release $O_2$ at a rate of 40 $g/m^2/day$ (17), resulting in biofixation of approximately 200 kg of $CO_2$ (18) and production of 100 kg of dry biomass (20) of seaweed origin (19).

To obtain seaweed biomass, the following steps are required:

a) adding ground drilling gravel to the concentrations ranging from 0.01% to 95%, preferably from 0.1%, based on mass/mass (kg/kg) or mass/volume (kg/L) units, containing in its chemical composition Al, Fe, Ca, Mg, Cu, Mn, Zn, Ni, Cr, P, K and Na in BG11 control culture medium or other culture medium or combinations of culture medium;

b) then, performing the inoculation of the strain (cyanobacteria, microalgae or macroalgae) in tanks or other types of transparent containers subjected to natural or artificial solar lighting (light intensity higher than 60 klux, ideally 120 klux), photoperiod from 8 to 14 hours, ideally 12 hours), in a low concentration of inoculum (ranging from 1 mg/L to 1 g/L, preferably about of 50 mg/L);

c) at the same time, carrying out another inoculation with similar concentration and under the same lighting conditions, using the same culture medium without drilling gravel, maintained as a control over time;

d) promoting bubbling to the system by aeration and $CO_2$ supply (without limitation of purity, preferably with 99% purity) through solenoid valve triggered by pH controller with electrochemical sensor (glass electrode), maintaining the pH between 6 and 7, preferably pH 6.5 over 3 to 12 days of growth, preferably 6 days. The salinity, measured with reference to the mass of sodium chloride, between 0.001 and 150 g/L, ideally 10 g/L. The temperature between 24 and 48° C., ideally at 34° C.;

e) performing daily observations under an optical microscope and also macroscopic observations to attest the presence of healthy microalgae growing in the bottle with culture containing gravel (P) and in the bottle with control culture (C).

A dynamic experiment was carried out with injection of $CO_2$ for observing the behavior of the microalgae *Desmodesmus* sp. The following abiotic parameters were defined: salinity 10 g/L, luminous intensity 120 klux (photoperiod 12 hours/day), temperature 34° C., pH 6.5 for sample with gravel and control.

Figure 7:
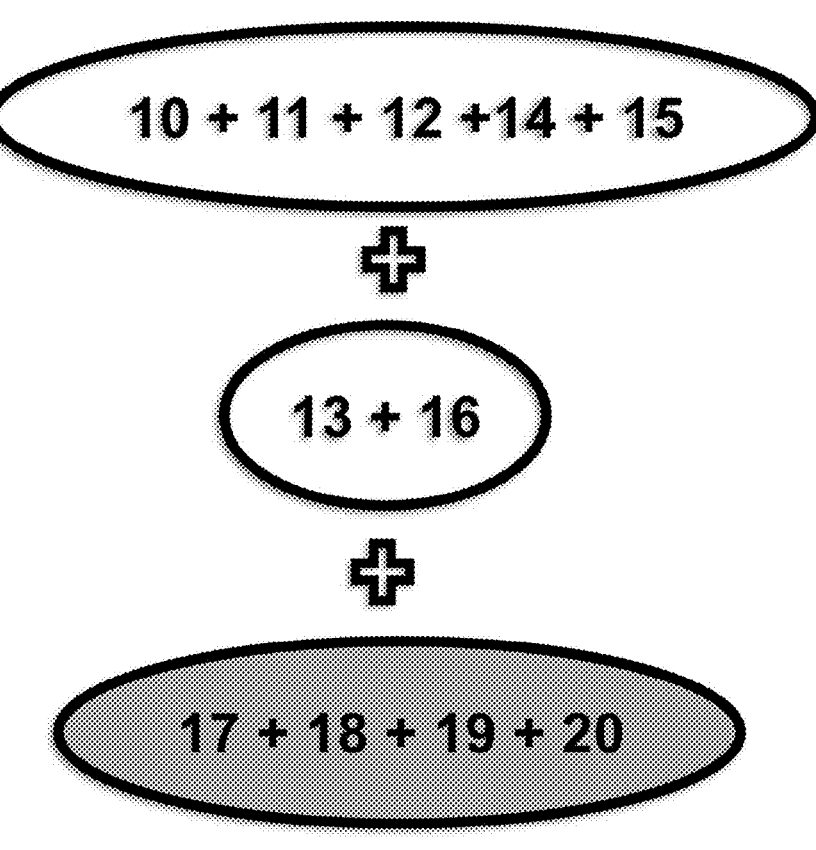
FIG. 7 illustrating the interconnection between the components of the invention.

The strain used grew by absorbing $CO_2$ and using the nutrients provided in the added mixture (drilling gravel+culture medium), allowing to obtain an increase in growth with increased productivity, as shown in FIG. 7.

Figure 2:
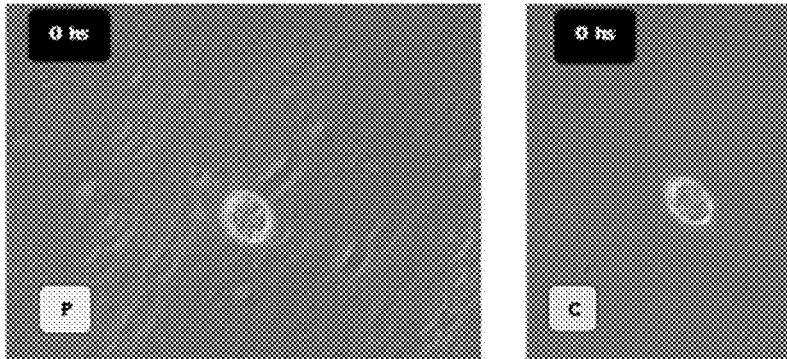
FIG. 2 illustrating the microalgae *Desmodesmus* sp. at the beginning of the experiment, after inoculation (1000× magnification), where (P) is the reactor with drilling gravels and (C) the control reactor.
Figure 3:
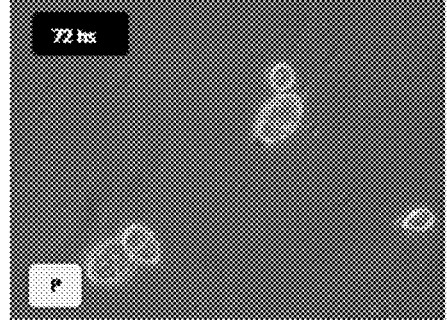
FIG. 3 illustrating the microalgae *Desmodesmus* sp. 72 hours from the start of the experiment (1000× magnification), where (P) is the reactor with drilling gravels and (C) the control reactor.
Figure 3:
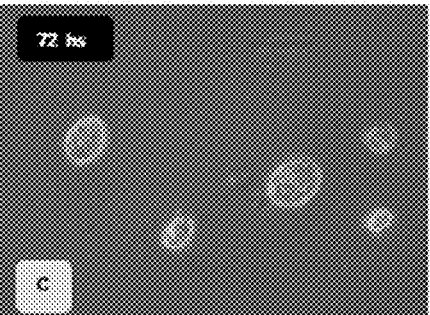
Figure 4:
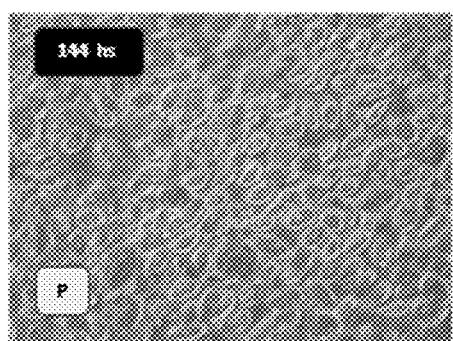
FIG. 4 illustrating the microalgae *Desmodesmus* sp. after 144 hours from the beginning of the experiment (1000× magnification), where (P) is the reactor with drilling gravels and (C) the control reactor.
Figure 4:
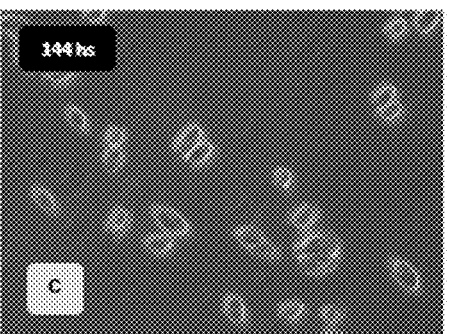
Figure 5:
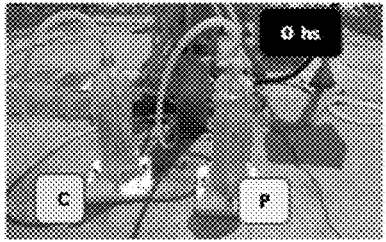
FIG. 5 illustrating the general appearance of the crops throughout the experiment with agitation and $CO_2$ injection, where the sample with addition of gravel is called (P) and the control sample is called (C)
Figure 5:
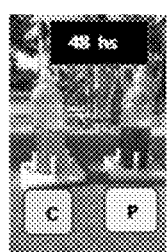
Figure 5:
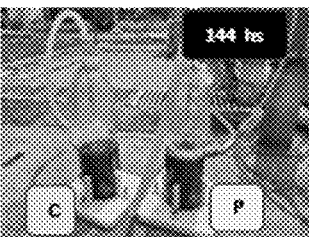
Figure 6:
FIG. 6 illustrating the general appearance of the crops two days after the end of the experiment, where the sample with the addition of gravel is called (P) and the control sample is called (C)

Daily observations under an optical microscope (FIGS. 2, 3 and 4) and macroscopic observations (FIG. 5) attested the presence of healthy microalgae (*Desmodesmus* sp) with growth in the bottle containing gravel (P) and in the bottle control (C). After the end of the experiment, the bottles containing the cultures were kept without agitation for a week, having shown high stability in microalgae of the control culture and in the microalgae that grew in the medium containing gravel (FIG. 6).

At the end of the experiment, it was found that there was excellent growth of *Desmodesmus* sp with $CO_2$ capture, using drilling gravel at a concentration of 1 g/L in BG11 culture medium. There was a difference observed across microscopy between the control sample and the sample containing gravel with regard to the amount of biomass generated. The sample containing gravel had a higher concentration cell with respect to the control sample.

Both samples were shown to contain cells in excellent physiological state in both conditions—with and without adding gravel to the culture medium. The microalgae *Desmodesmus* sp has demonstrated affinity with the culture medium containing this type of solid residue, which represents an innovative result in relation to the international literature. Quantitative experiments are needed to better understand the growth rates obtained by *Desmodesmus* sp subjected to contact with the gravel.

The present invention is not based on the $CO_2$ biofixation, which generally occurs by microalgae, autotrophic macroalgae and cyanobacteria based on photosynthesis. The invention derives from the fact that these organisms have a higher growth rate when there is drilling gravel in the medium compared to the control sample. As a result, there will be a higher rate of $CO_2$ biofixation and consequently greater production of biomass, leading to productivity benefits and operational lower costs and investment in crops associated with oil and gas industry.

It is worth noting that productivity is directly related to the area required for the microalgae culture. The higher the productivity achieved in the microalgae culture, the smaller the area required in the production tank installation and, consequently, the investment cost for implementing the technology.

Experiments were carried out that proved the good growth of microalgae (of various genera and species) under different cultivation conditions with the mixture of drilling gravel from oil wells and conventional culture medium, having been obtained excellent biomass quality for use with several purposes. There was an injection of $CO_2$ throughout the cultures, proving the intensive biofixation of this compound over the course of algae growth. As mentioned above, the increase in productivity of algae biomass cultured with gravel drilling of E&P activities constitutes a process, which is the main object of the present invention.

It should be noted that, although the present invention has been described in relation to the attached drawings, this may undergo modifications and adaptations by persons skilled in the art, depending on the specific situation, but provided that it is within the inventive scope defined herein.

The invention claimed is:

1. A method for producing seaweed biomass, comprising:
adding ground drilling gravel in a concentration ranging from 0.01% to 95% based on mass/mass (kg/kg) or mass/volume (kg/L) units to a culture medium to form a gravel-containing culture medium, wherein the ground drilling gravel comprises Al, Fe, Ca, Mg, Cu, Mn, Zn, Ni, Cr, P, K, and Na;
inoculating a first sample of macroalgae and microalgae in the gravel-containing culture medium at a concentration ranging from 1 mg/L to 1 g/L in a first transparent container subjected to natural or artificial sunlight with luminous intensity greater than 60 klux for 8 to 14 hours;
inoculating a second sample of the macroalgae and microalgae in a control medium comprising the culture medium without the ground drilling gravel at a concentration of 1 mg/L to 1 g/L in a second transparent container subjected to natural or artificial sunlight with luminous intensity greater than 60 klux for 8 to 14 hours;
supplying $CO_2$ to each sample through a solenoid valve triggered by a pH controller with an electrochemical sensor comprising a glass electrode, wherein a pH of each sample is maintained between 6 and 7, over 3 to 12 days of growth; a salinity of each sample, measured with reference to a mass of sodium chloride, is maintained between 0.001 and 150 g/L; and a temperature of each sample is maintained between 24 and 48° C.; and
performing daily observations under an optical microscope and macroscopic observations to attest a presence of healthy microalgae growing in the gravel-containing culture medium and in the control medium.

2. The method of claim 1, wherein the concentration of the ground drilling gravel is 0.1%.

3. The method of claim 1, wherein the first sample and/or the second sample comprises cyanobacteria.

4. The method of claim 1, wherein the inoculation of the first sample and/or the second sample is carried out at a concentration of 50 mg/L.

5. The method of claim 1, wherein the control culture medium is BG11.

6. The method of claim 1, wherein the first transparent container and/or the second transparent container is subjected to natural or artificial sunlight with luminous intensity of 120 klux for 12 hours.

7. The method of claim 1, wherein the $CO_2$ comprises 99% purity.

8. The method of claim 1, wherein the pH of each sample is 6.5, over 6 days of growth.

9. The method of claim 1, wherein the salinity of each sample, as measured with reference to the mass of sodium chloride, is 10 g/L.

10. The method of claim 1, wherein the temperature of each sample is 34° C.

* * * * *